US008758019B2

(12) United States Patent
Suzansky

(10) Patent No.: US 8,758,019 B2
(45) Date of Patent: Jun. 24, 2014

(54) MULTIMEDIA GAME BASED SYSTEM AND PROCESS FOR MEDICAL, SAFETY AND HEALTH IMPROVEMENTS

(76) Inventor: James W. Suzansky, Long Valley, NJ (US)

(*) Notice: Subject to any disclaimer, the term of this patent is extended or adjusted under 35 U.S.C. 154(b) by 898 days.

(21) Appl. No.: 11/498,708

(22) Filed: Aug. 3, 2006

(65) Prior Publication Data

US 2008/0032267 A1 Feb. 7, 2008

(51) Int. Cl.
A63B 69/00 (2006.01)
G06F 19/00 (2011.01)
G06Q 50/20 (2012.01)
G06Q 50/24 (2012.01)
A61B 5/00 (2006.01)
G09B 23/28 (2006.01)

(52) U.S. Cl.
CPC .......... *G06F 19/3481* (2013.01); *G06F 19/322* (2013.01); *G06F 19/3418* (2013.01); *G06F 19/324* (2013.01); *G06F 19/363* (2013.01); *G06F 19/3425* (2013.01); *G06F 19/3456* (2013.01); *G06F 19/3475* (2013.01); *G06Q 50/20* (2013.01); *G06Q 50/24* (2013.01); *Y10S 128/92* (2013.01); *A61B 5/0022* (2013.01); *G09B 23/28* (2013.01)
USPC .......................................... 434/247; 128/920

(58) Field of Classification Search
CPC ....... G06Q 50/22; G06Q 50/24; G06Q 10/10; G06F 19/3418; G06F 19/322; G06F 19/3481; G06F 19/345; G06F 19/363; G06F 19/324; G06F 19/3425; G06F 19/3431; G06F 19/3456; G06F 19/3475; Y10S 128/92; A61B 5/0022; G09B 23/28

USPC ......................................................... 434/238
See application file for complete search history.

(56) References Cited

U.S. PATENT DOCUMENTS

| 5,601,435 | A | | 2/1997 | Quy | 434/307 |
| 5,722,418 | A | * | 3/1998 | Bro | 600/545 |
| 5,879,163 | A | | 3/1999 | Brown et al. | 434/236 |
| 6,139,494 | A | * | 10/2000 | Cairnes | 600/300 |
| 6,151,586 | A | | 11/2000 | Brown | 705/14 |
| 6,186,145 | B1 | | 2/2001 | Brown | 128/897 |
| 6,210,272 | B1 | | 4/2001 | Brown | 463/1 |

(Continued)

FOREIGN PATENT DOCUMENTS

| JP | 2005-049671 | 2/2005 | G09B 5/02 |
| WO | WO 2002/072211 | 9/2002 | A63B 22/06 |
| WO | WO 2005/020121 | 3/2005 | G06F 19/00 |

OTHER PUBLICATIONS

Internet Archive Wayback Machine, WebMD.com, Dec. 27, 2005, Internet Archive Wayback Machine, p. 1-60.*

(Continued)

*Primary Examiner* — Jack Yip
(74) *Attorney, Agent, or Firm* — Ernest D. Buff and Associates, LLC; Ernest D. Buff; Harry Anagnos

(57) ABSTRACT

A multimedia system and method provide self-improvement guidance in health, education, or safety. The user receives content material related to self-improvement, tracking of self-improvement behaviors, alerts to potential health dangers, and help information. A variety of games and puzzles guide and motivate the user through an educational process where the user's responses affect the sequencing of the testing. The user's interactions with the system are recorded and summarized.

60 Claims, 25 Drawing Sheets

(56) References Cited

U.S. PATENT DOCUMENTS

| | | | |
|---|---|---|---|
| 6,260,022 B1 | 7/2001 | Brown | 705/2 |
| 6,450,820 B1 | 9/2002 | Palsson et al. | 434/236 |
| 6,554,618 B1* | 4/2003 | Lockwood | 434/322 |
| 6,561,811 B2 | 5/2003 | Rapoza et al. | 434/236 |
| 6,918,769 B2 | 7/2005 | Rink | 434/247 |
| 7,301,463 B1* | 11/2007 | Paterno | 340/573.1 |
| 7,762,264 B1* | 7/2010 | Ramig et al. | 128/898 |
| 2002/0055386 A1 | 5/2002 | Yotsugi et al. | 463/42 |
| 2002/0082865 A1 | 6/2002 | Bianco et al. | 705/2 |
| 2002/0187463 A1* | 12/2002 | Aspe et al. | 434/362 |
| 2003/0050537 A1 | 3/2003 | Wessel | 600/300 |
| 2003/0087218 A1* | 5/2003 | Brown et al. | 434/116 |
| 2003/0153819 A1* | 8/2003 | Iliff | 600/300 |
| 2003/0208380 A1* | 11/2003 | Honeycutt | 705/2 |
| 2004/0171460 A1* | 9/2004 | Park | 482/8 |
| 2004/0180708 A1 | 9/2004 | Southard et al. | 463/1 |
| 2004/0260577 A1* | 12/2004 | Dahlin et al. | 705/2 |
| 2005/0060205 A1* | 3/2005 | Woods et al. | 705/4 |
| 2005/0131738 A1 | 6/2005 | Morris | 705/2 |
| 2005/0197545 A1* | 9/2005 | Hoggle | 600/300 |
| 2005/0283385 A1* | 12/2005 | Hunkeler et al. | 705/2 |
| 2006/0089542 A1* | 4/2006 | Sands | 600/300 |
| 2006/0105825 A1 | 5/2006 | Findlay | 463/4 |
| 2006/0204942 A1* | 9/2006 | Kimball | 434/307 R |
| 2007/0072156 A1* | 3/2007 | Kaufman et al. | 434/236 |
| 2008/0177578 A1* | 7/2008 | Zakim | 705/3 |
| 2008/0268413 A1* | 10/2008 | Leichner | 434/262 |

OTHER PUBLICATIONS

WebMD Health Services, WebMD Personal Health Manager Employee Messaging Guide, Dec. 2005, WebMD Health Services, p. 1-16.*

WebMD Health Services Group, Health and Benefits Manager, Jun. 2004, WebMD Health Services Group, p. 1-8.*

"The Game Closet", found at http://www.kidshealth.org/kid/closet/, Jun. 5, 2006, pp. 1-4.

"A Trusted Partner", found at http://www.globalmedic.com/L2/index.jsp, Jun. 5, 2006, pp. 1-2.

"Native Dancer Diabetes Education Project", found at http://www.nativedancerndsu.edu/home/, Jun. 5, 2006, pp. 1-2.

* cited by examiner

SOME MYTHS ABOUT DIABETES

An Interactive Game For Your Cellphone

Figure 4A

What you can play while you learn

- Select the kind of maze game you would like to play – highlight it and press OK
  – Getting out of a haunted house
  – Getting through a corn field
  – Walking through a garden

Figure 4B

You have selected the Haunted House Maze – Press the OK key now if you want to skip the game instructions

- You will use your phone's number keys to play this game
- When you are asked a question, press the number for the answer you think is correct
- Use the OK key to move to the next text screen

Figure 4C

Maze Game Instructions

- The objective is to get out of the house by the shortest path – that means with the fewest mistakes in your choices
- Each step will begin with some information about diabetes
- You will get a choice of several answers to a question, each matched to a door out of your current location in the maze
- Choosing the correct answer number on your phone will move you in the right direction to get out

Figure 4D

Maze Game Mistakes

- Choosing a wrong answer number on your phone will move you into another room with new material to read and doors to choose
- When you get the right answer, you will get back on track to leave the house
- Choosing a wrong answer will take you deeper into the house to try again

Figure 4E

Maze Game Finish

- Just before you leave the house, you will get a few questions in a row
- Get all right and you are out, but make a mistake and you move back into the house to try again
- When you are out, you will get your score and the best score possible
- The lower the better so try again until you get to the lowest score possible!

Figure 4F

Myth 1 (Room 1)
You can catch diabetes from someone else

Figure 4G

NO! (Room 1)

- Diabetes is not contagious
- You cannot catch it from being near others who already have it
- You cannot catch it from contaminated food or water
- You cannot catch it by breathing bad air

Figure 4H

(Exiting Room 1)
You can avoid catching diabetes by:

1. Always washing your hands every hour
2. You cannot "catch" diabetes
3. Only eating with family members
4. Staying out of backwoods areas

Figure 4I

**(Number 2 Selected)
RIGHT!**

- Image of moving from Room 1 to Room 2

Figure 4J (Number 1, 3 or 4 Selected)
Try Again
(Move to New Room 1B)

- You cannot catch diabetes from another person
- You can't get it from contaminated air, food or water
- No amount of cleanliness will prevent diabetes

Figure 4K (Exiting Room 1B)
You can avoid catching diabetes by:

1. Wearing surgical masks
2. Starting an all vegetable diet
3. You cannot "catch" diabetes
4. Washing your hands before each meal

Figure 4L (Number 3 Selected)
RIGHT!

- Image of moving from Room 1B to Room 2

Figure 4M (Number 1, 2 or 4 Selected)
NO!

(Element 1 Info 1 Repeated after moving back to Room 1; Then same following navigation)

- Diabetes is not contagious
- You cannot catch it from being near others who already have it
- You cannot catch it from contaminated food or water
- You cannot catch it by breathing bad air

Figure 4N

Myth 2 (Room 2)
People with diabetes can't eat sweets
- like cake or chocolate

Figure 4O

No Again! (Room 2)

- Sweets can be a part of a diabetic's diet plan
- They are not forbidden for diabetics
- They should be combined with a healthy exercise plan
- Managing your overall weight and health is what's important

Figure 4P

(Exiting Room 2)
For sweets in a diabetic diet

1. Expect nothing but trouble
2. Plan them as part of the total meal plan
3. Allow 1 hour of running for each piece of chocolate
4. Plan only totally organic sweets

Figure 4Q

- (Number 2 Selected) RIGHT!
- Image of moving from Room 2 to Room 3

Figure 4R (Number 1, 3 or 4 Selected
Move to new Room 2B)
Try Again – Remember that

- Diabetes influences your diet
- BUT there is a lot you can do to manage it
- AND that includes being able to continue eating most of your favorite foods

Figure 4S

(Exiting Room 2B)
You cannot eat sweets as part of a diabetic's diet

1. True
2. False

Figure 4T (Number 2 Selected)
RIGHT!

- Image of moving from Room 2B to Room 3

Figure 4U (Number 1 Selected –Element 2 Info 1 Repeated after moving back to Room 2; Then same following navigation)

It is TRUE!

- Sweets can be a part of a diabetic's diet plan
- They are not forbidden for diabetics
- They should be combined with a healthy exercise plan
- Managing your overall weight and health is what is important

Figure 4V

MULTIMEDIA GAME BASED SYSTEM AND PROCESS FOR MEDICAL, SAFETY AND HEALTH IMPROVEMENTS

BACKGROUND

1. Field of the Invention

The present invention is directed to programs for improving the lifestyle of consumers through medical, safety, and health education; and more particularly, to a system and process for providing health information and assistance, in an entertaining manner, through online gaming.

2. Description of the Related Art

Most members of the general public would benefit from a better overall understanding of health and medicine. With adequate health education, patients are able to maintain a healthy lifestyle and deal more effectively with diseases and illnesses. Presently, print literature, books, magazines, and online health websites provide the consumer with information on a variety of health topics and issues. Nevertheless, many individuals remain uninformed and continue to lead unhealthy lifestyles characterized by obesity, drug addiction, smoking and unsafe driving practices.

Patients need to be motivated and supported, in a manner which is psychologically appealing, to achieve better medical management, safety, and health maintenance. There exists a need for an interactive, multimedia, entertaining system and method that will provide effective health education by creating enthusiasm for self-instruction. Such a gaming system must ensure learning by rewarding correct responses and providing further instruction when learning has not taken place. To create maximum motivation, there exists a need for games of this kind which appeal to specific demographic groups.

Today's patient is also an involved patient so there exists a need for information about the causes and treatments of illness as well as the resources for obtaining additional information and coping with the emotional and logistical problems illness brings. Today's consumer is tech-savvy and demands speed, convenience and ease-of-use in the consumer's daily activities. Accordingly, there remains a need for a system that can provide health and safety information on-the-go, in a portable manner, and be effectively integrated with the consumer's other technology products.

In addition to requiring convenience, the consumer can only succeed in achieving a healthier lifestyle when the consumer is able to track the consumer's personal progress toward health goals. As the number of people with chronic conditions, such as diabetes, high blood pressure and obesity rises, there is an ever-increasing need for a system and procedure to store the individual's history of blood glucose levels, body fat, salt intake, and the like. Likewise, individuals need to track if they are making progress towards personal goals such as weight loss, lowered cholesterol, and increased bone mass.

As the population continues to age, the ability to track medications, dosages, contra-indications to medications, and refill expiration is an ever-increasing requirement. There is a need for children of the elderly to be able to monitor their parents' compliance with medication regimes, as dementia and ill-health begin to affect their parents' mental abilities. There is also a need for a system which will alert the patient, or a concerned relative, if a potentially dangerous medical condition exists.

With the increasing bureaucratization of health care, patients need assistance when interfacing with the insurance community. There is a need for a system which will help patients complete insurance forms correctly, make correct decisions regarding insurance, and understand how to proceed with an insurance claim. There is a general need to supply a two-way contact process for patients regarding today's complex health care issues.

There is also a need to better understand how the general public deals with health and safety improvement and why attempts at living a healthy lifestyle are often unsuccessful. Toward this end, a system for recording and summarizing the individual's efforts toward achieving a health benefit is necessary. Presently, there is no single system or method which provides the above-mentioned needs in a manner which the public will realistically embrace.

SUMMARY OF THE INVENTION

The present invention discloses a system and method for providing a user with self-improvement guidance in health, education, or safety wherein a gaming portion: 1) tests the user's knowledge of the content material; 2) the user's responses to the test questions determine the sequence of the game; and 3) when a response is incorrect, the user is continually presented with content material until the user answers the question correctly. A monitoring feature tracks the user's self-improvement behavior, so that progress toward self-improvement can be evaluated. An alerting feature alerts the user to problem behaviors revealed by the monitoring feature. An educating feature provides content material and sources for identifying additional content. An interactive feature provides the user with a variety of helpful information through a variety of media for maximum user convenience. The information developed by the system is memorialized by a recording feature for recording the user's interactions with the system and success with improvement.

BRIEF DESCRIPTION OF THE DRAWINGS

The invention will be more fully understood and further advantages will become apparent when reference is made to the following detailed description of the preferred embodiments of the invention and the accompanying drawings, in which like numerals refer to like parts, and in which:

FIGS. 4A-4V are exemplary screen shots illustrating the gaming portion of the present invention.

DETAILED DESCRIPTION OF THE INVENTION

It is to be understood that the figures and descriptions of the present invention have been simplified to illustrate elements that are relevant for a clear understanding of the present invention, while eliminating, for purposes of clarity, many other elements found in a typical multimedia system. Those of ordinary skill in the art will recognize that other elements are desirable and/or required in order to implement the present invention. However, because such elements are well known in the art, and because they do not facilitate a better understanding of the present invention, a discussion of such elements is not provided herein.

Figure 1:
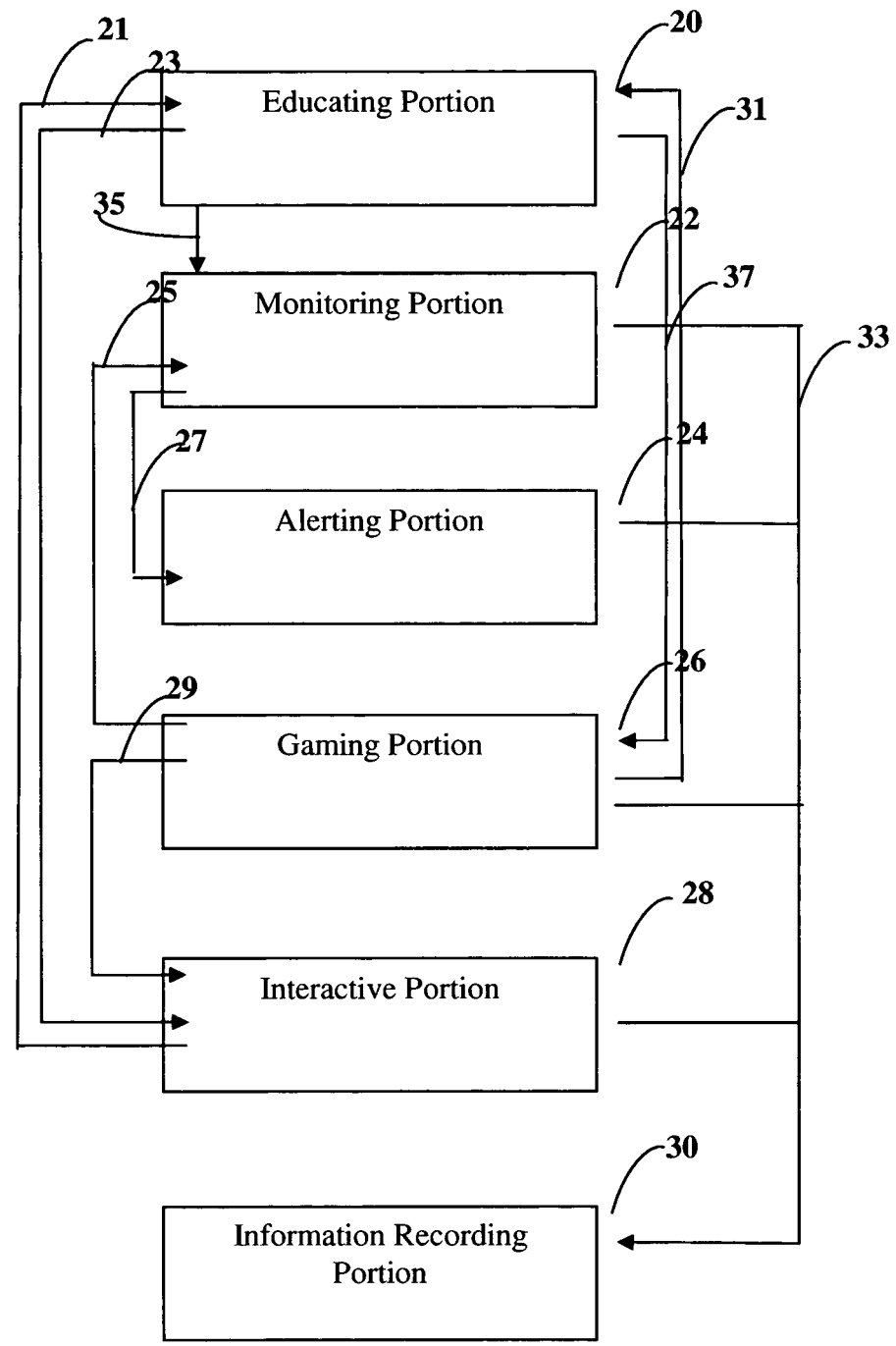
FIG. 1 is a block diagram of the present invention illustrating the flow of the system.

FIG. 1 is a diagram of the information flow of the present invention indicating the components of the system and how information passes between each component. The invention, which is especially suited for use by the general public, comprises a multimedia system and process for medical, safety, and health improvements. The system incorporates psychological principles into the structure of gaming to educate, support, and motivate participants to improve their safety, medical management, and health maintenance. While print information and websites provide the public with information on a variety of health topics and issues, they lack the motivating features and entertainment value of the present invention. The current obesity epidemic, the number of smokers, and the prevalence of high blood pressure speak to the need for a system, which can successfully engage the public in pursuing self-improvement.

The educating portion 20 provides both general and specific content information on topics related to health, medicine and safety. So, for example the educating portion 20 provides information on specific diseases such as diabetes, its causes, symptoms, and treatments as well as where to find additional helpful information. The educating portion also provides very specific information, such as how to measure blood glucose levels, body mass index, or pulse rate. Furthermore, the educating portion 20 also discusses more general topics such as weight loss, and how to lower blood pressure and cholesterol.

The monitoring portion 22 monitors the user's compliance with standard health guidelines, described in the educating portion 20, 35. These guidelines include, for example, following a recommended diet, moderating alcohol intake, observing medical contra-indications, and exercising daily. The user selects the guidelines the user wishes to have monitored and inputs the user's standard physiological measures of wellness, such as weight and blood pressure. The monitoring portion 22 tracks the user's progress towards health goals the user identifies, such as achieving weight loss or maintaining blood glucose levels. The monitoring portion further tracks information such as whether the patient is taking the correct medication dosage, if medical appointments have been kept, and whether a refill on a prescription is needed. The user manually inputs and updates information such as medication dose taken, blood glucose level, weight etc. to the monitoring portion 22 so that progress toward wellness can be tracked based on divergence from the baseline inputs. Alternatively, such data may be input directly from devices which generate physiological measurements such as a peak flow meter or ECG, for example, or from devices that record dispensing a dose of medication. Children of aged parents and others are able to obtain access to the monitoring portion 22 to help ensure that guidelines are being followed.

The monitoring portion 22 provides information to the alerting portion 24, 27 so that the user can be notified when a potentially dangerous situation exists. The monitoring portion draws upon standard medication contraindications, associated with the drug prescription information the user has entered, as well as physiological danger measures, reflected in standard guidelines such as the blood pressure range chart. So, for example, if blood levels of glucose or pulse rate are too high, the user or other relatives will be notified. Similarly, if the user is engaging in an unsafe behavior, such as taking two drugs which interact dangerously or failing to complete a prescribed dosage of medication, an alert is issued.

The gaming portion 26 interacts with the educating portion 20, 31, 37 to provide motivational activities, such as games and puzzles, containing content relevant to medical management, safety, and health maintenance. The gaming portion is delivered over a variety of media for maximum user convenience, and designed to make health fun and enhance the attention, learning, and motivation of participants. The gaming portion comprises games and puzzles targeted to work most effectively with a variety of demographic groups such as children, pre-teens, seniors, sports enthusiasts, special needs groups, or highly mobile individuals. An algorithm is employed to automatically match the user's demographics with the appropriate games or the user selects the games of interest. Games may take the form of mazes, shooting games, assembly and/or matching games, and the like.

Basic psychological principles of learning are employed, in a programmed instruction format, to provide participants with health and medical information in an easy-to-acquire and understand process. Game format includes multiple choice questions wherein the user's answer choice directly impacts the outcome and flow of the game. To excel at a game, the user must answer all the questions correctly.

The interactive portion 28 communicates with the educating portion 20 to connect the user 23, 21, via hyperlinks, with websites containing further information on health and safety topics. Examples include links to key websites such as the American Diabetes Association, a specific drug website, a specific pharmaceutical website and the like. The gaming portion 26 also communicates 29 with the interactive portion 28 so that the user may search the Web for information necessary to complete a game. Through the interactive portion 28, the user is provided with a two-way contact process to secure information or assistance. This includes live support directed at a variety of health issues including insurance claims assistance, prescription refill, or physician referral. In addition, the interactive portion includes a search feature enabling the user to search the system or the Web. Expanded cell phone information sources will also become part of the easily linked information.

The information recording portion 30 records information 33 generated by the monitoring portion 22, alerting portion 24, gaming portion 26, and interactive portion 28. This information includes personal information input by the user through the monitoring portion 22 such as name, address, age, gender, and physician. It also includes information acquired from the monitoring portion 22 such as prescription numbers, dosages, effects of medication the user has taken, health goals, and the like. It further includes a record of the user's gaming activities, acquired from the gaming portion 26 indicating the user's level of health knowledge. It further includes a record of the user's help requests, generated by the interactive portion 28, indicating content areas of interest to the user. It also includes health and safety problems the user has experienced as recorded by the alerting portion 24. The information recording portion 30 summarizes this information, gathered from the participation of its users, and makes this information available as a service to assist health, safety and medical providers, such as pharmaceutical companies, specific disease foundations, security services, and public and private support agencies.

Figure 2:
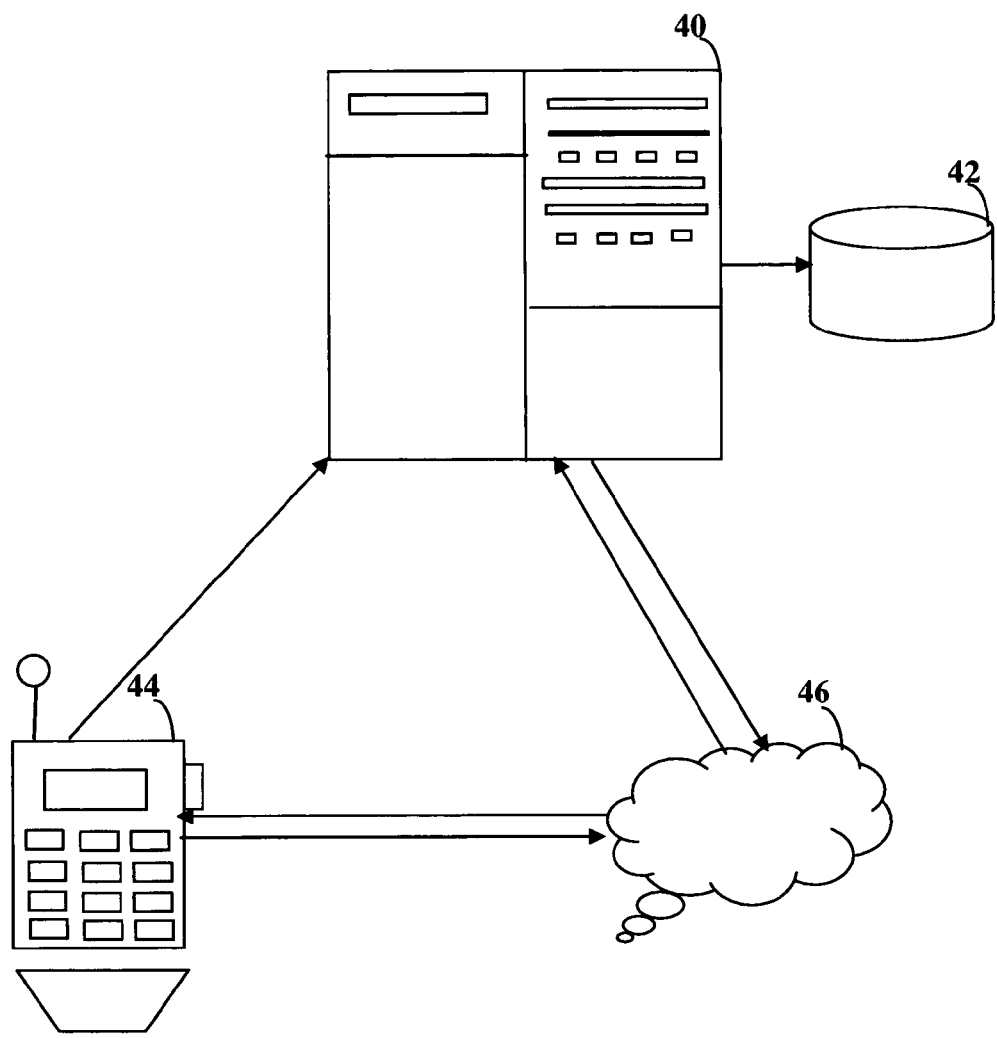
FIG. 2 is a diagram of the system of the present invention.

FIG. 2 is a diagram of the system of the present invention. The user interacts with the system server 40 using a communication device such as a cell phone 44. Accordingly, participation in the gaming portion 26 of the system, or the interactive portion of the system 28, requires no special effort on the user's part or deviation from normal every-day routine. Young people, who use phones for text messaging and a variety of multimedia applications are particularly at home with the system, which uses the phone's key pad to interact with the gaming portion. Likewise, sports enthusiasts and other highly mobile individuals find it easy to update their information, using the monitoring portion 22.

As an alternative communication device 44, the system uses a personal digital assistant, computer, kiosk, or other wired or wireless standard communication device. The systems server 40 may be a remote computer, a local computer, a chip installed within the communication device, or other digital processing software or hardware. The storage medium, used by the information recording portion 30, may be local or remote and take the form of disk, flash memory, tape, cartridge, or any other standard storage media. The system content information and recorded information may be stored remotely on a website 46.

The user may interact with the server 40 and website 46 in a wired or wireless fashion. Alerts from the alerting portion 24 and information from the educating portion 20 may likewise be obtained from local or remote storage. The system may exist stand-alone or networked with other devices.

Figure 3:
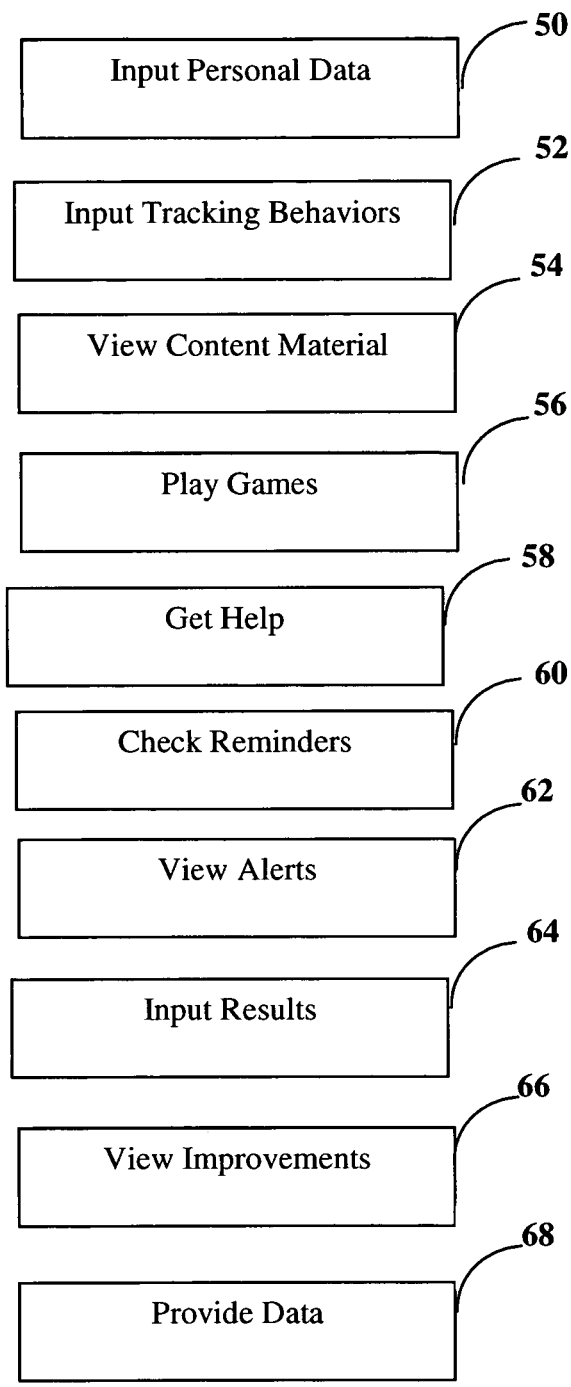
FIG. 3 is a block diagram illustrating the method of the present invention.

FIG. 3 displays the method of the present invention. In step 50, the user inputs personal data such as name, gender, age, physician, prescription numbers, medical or health conditions, insurance company, relatives to be alerted in the event of health crises, and the like. In step 52, the user inputs the lifestyle behaviors, which the user would like to track. These can include, for example, calories consumed, weight, blood glucose level, body mass index and bone density. The user also inputs required medication doses or this information is obtained automatically from the prescription information.

In step 54, the user views content material related to medical care, health and safety. This material may take the form of a website or be incorporated into a game. In step 56, the user plays a game, which includes multiple choice questions on health and safety topics, wherein the user's answer choice directly impacts the outcome and flow of the game. The user is presented with content material, provided by step 54, and then responds to questions which test the user's knowledge and understanding of the material presented. The greater the number of questions the user answers correctly on the first try, the higher the user's score and the more quickly the user finishes the game. The games presented will be designed to appeal to the user's demographic profile.

In step 58, the user may choose to receive help and assistance. Help takes the form of website FAQs, real-time interaction with a help desk representative, questions emailed, context-sensitive help accessible through a programmed key, and other standard help formats. In step 60, the user may choose to check reminders related to the user's help behaviors. For example, the user may be reminded to refill a prescription, take a medication, or submit an insurance form. In step 62 the user views alerts notifying the user of potentially dangerous medical or safety situations. For example, the user may have taken an incorrect dosage, be taking two drugs which interact dangerously or have recorded alcohol intake, when this is contraindicated based on the user's medication regime. The alerts appear automatically but the user may also view alerts electively, at any time, as well as deactivate the alert feature. The user may also grant permission to a third party, such as a relative, to participate in viewing the alerts.

In step 64, the user inputs physiological measures, which reflect the results of medication taken or changes in lifestyle. For example, if the user has been exercising, the user updates the user's weight or blood pressure, for example, to measure the effects of this wellness behavior. If the user suffers from a medical condition, such as diabetes, the user inputs the user's glucose level. An analysis of the results input, in step 64, are then viewed in step 66. The system records information using the information recording portion 30 so the user can view the history of the user's progress toward wellness. So, for example, the user can view the user's glucose levels, for every day in the past month, weight gain, over the past six months and so on. In step 68, the information is summarized and made available to health, safety and medical providers. This information provides a highly detailed view of the wellness behavior of consumers, which would not otherwise be readily available.

FIGS. 4A-4V are sample screen shots, illustrating an example of the game format, which the user views via the gaming portion 26. Formats follow the general pattern of: 1) presenting a myth about a disease or condition; 2) providing information to dispel the myth; 3) testing the user to determine whether the user has understood and assimilated the information; 4) if the user answers correctly, notifying the user and moving to the next topic; 5) if the user answers incorrectly, notifying the user and repeating the information already provided to dispel the myth; and 6) retesting the user. Through this programmed learning format, which provides instant feedback, the user is motivated to continue learning the material. The text screens of the Figures would be included in images of rooms in a house, for example, with game and learning progress shown by advancing through the house and eventually out of it.

What is claimed is:

1. A multimedia system based on gaming experiences for providing a user with self-improvement guidance in health, education, or safety to achieve a specific predetermined goal, the multimedia system includes computer instructions embodied on a non-transitory computer-readable medium to be executed by a processor, the computer instructions comprising:
  a) an educating portion for communicating content material related to the self-improvement guidance;
  b) a monitoring portion for improving and tracking specific self-improvement behaviors identified by the user, the user inputting into the monitoring portion the user's physiological characteristics, selected from a set of standard wellness measures;
  c) an alerting portion for alerting the user to potential health dangers revealed by the monitoring portion;
  d) a gaming portion for improving and testing the user's knowledge of the content material, in which the user's responses to game steps must indicate understanding and assimilation of the information covered by a particular topic before proceeding to additional topics, said topics being selected by said multimedia system in order for said user to achieve said specific predetermined goal, a format of the gaming portion being selected to reflect the user's demographics, based upon a matching algorithm, which matches a profile of the user with available game formats;
  e) an interactive portion for providing help information to the user; and
  f) an information recording portion for recording the user's interaction with the system;
  whereby said multimedia system creates an entertaining environment in which predetermined goals can be achieved;
  g) further including the step of inputting to the monitoring portion:
    1) prescription information;
    2) each dose of medication the user has taken; and
    3) the effects of the dose on the user's:
      a) levels of pre-defined bodily fluids or
      b) measurements of pre-defined bodily functions;
  h) said self-improvement behaviors further comprise compliance with a medication regime.

2. The system of claim 1 wherein the medication regime further comprises at least one prescribed medication dosage for at least one medical condition.

3. The system of claim 1 wherein the gaming portion is a maze.

4. The system of claim 1 wherein the gaming portion is a puzzle.

5. The system of claim 1 wherein the gaming portion is a shooting game.

6. The system of claim 1 wherein the gaming portion is a matching game.

7. The system of claim 1 wherein the gaming portion is an assembly game.

8. The system of claim 1 wherein the gaming portion requires the user to answer multiple choice questions correctly, in order to progress toward the finish of the game.

9. The system of claim 8 wherein the educating portion continues to present the user with content information, pertaining to each multiple choice question answered incorrectly, until the user answers the question correctly.

10. The system of claim 1 wherein the user interacts with the gaming portion using a cellular phone.

11. The system of claim 1 wherein the user interacts with the gaming portion using a kiosk.

12. The system of claim 1 wherein the user interacts with the gaming portion using a personal digital assistant.

13. The system of claim 1 wherein the user interacts with the gaming portion using a wireless device.

14. The system of claim 1 wherein the content of the educating portion is displayed on a dedicated website.

15. The system of claim 14 wherein the interactive portion provides a search feature of the website and the Internet.

16. The system of claim 1 wherein the interactive portion provides hyperlinks to websites related to the content material of the educating portion.

17. The system of claim 1 wherein the content material of the educating portion offers guidance for treatment of specific diseases.

18. The system of claim 1 wherein the content material of the educating portion offers guidance for treatment of specific medical conditions.

19. The system of claim 1 wherein the content material of the educating portion provides guidance for tracking standard healthy behaviors and their results.

20. The system of claim 1 wherein the content material of the educating portion displays procedures for performing a predefined set of disease-specific self-tests of body fluids.

21. The system of claim 1 wherein the content material of the educating portion displays guidelines for a predefined set of disease-specific medication dosages and contra-indications for these dosages.

22. The system of claim 1 wherein the alerting portion reads the information captured by the monitoring portion and tracks it.

23. The system of claim 22 wherein the alerting portion alerts the user when it is time to refill a prescription.

24. The system of claim 22 wherein the alerting portion notifies the user if the user fails to take the proper dosage in accordance with the prescription.

25. The system of claim 1 wherein the interactive portion provides the user with information and assistance stored by the educating portion.

26. The system of claim 25 wherein the information and assistance is directed at filing insurance claims.

27. The system of claim 26 wherein the user's personal information, self-improvement behavior input to the monitoring portion, and responses to the gaming portion are recorded by the recording portion.

28. The system of claim 27 wherein the information recorded is provided as a service to assist health, security and medical providers.

29. The system of claim 1 wherein the self-improvement behaviors input to the monitoring system are chosen from a set of standard nutrition, exercise, and medication wellness practices.

30. The system of claim 1 wherein the alerting portion notifies the user of contraindications to the medication dosage the user is taking.

31. A multimedia method based on gaming experiences for providing a user with self-improvement guidance in health, education, or safety to achieve a specific predetermined goal, the multimedia method is implemented by computer instructions embodied on a non-transitory computer-readable medium to be executed by a processor, the multimedia method comprising the steps of:
  a) providing content material related to the self-improvement guidance through an educating portion;
  b) tracking specific self-improvement behaviors identified by the user through a monitoring portion, the user inputting to the monitoring portion the user's physiological characteristics, selected from a set of standard wellness measures;
  c) alerting the user to potential health dangers revealed by the monitoring portion through an alerting portion;
  d) testing the user's knowledge of the content material, through a gaming portion in which the user's responses to game steps must indicate understanding and assimilation of the information covered by a particular topic before proceeding to additional topics, said topics being selected in order for said user to achieve said specific predetermined goal, a format of the gaming portion being selected to reflect the user's demographics, based upon a matching algorithm, which matches a profile of the user with available game formats;
  e) providing help information to the user through an interactive portion; and
  f) recording the user's progress through an information recording portion;
  whereby said multimedia method promotes the achievement of predetermined goals in an entertaining environment;
  g) further including Lite step of inputting to the monitoring portion:
    1) prescription information;
    2) each dose of medication the user has taken; and
    3) the effects of the dose on the user's:
      a) levels of pre-defined bodily fluids or
      b) measurements of pre-defined bodily functions;
  h) said self-improvement behaviors further comprise compliance with a medication regime.

32. The method of claim 31 wherein the medication regime further comprises at least one prescribed medication dosage for at least one medical condition.

33. The method of claim 31 wherein the gaming portion is a maze.

34. The method of claim 31 wherein the gaming portion is a puzzle.

35. The method of claim 31 wherein the gaming portion is a shooting game.

36. The method of claim 31 wherein the gaming portion is a matching game.

37. The method of claim 31 wherein the gaming portion is an assembly game.

38. The method of claim 31 wherein the gaming portion requires the user to answer multiple choice questions correctly, in order to progress toward the finish of the game.

39. The method of claim 38 wherein the educating portion continues to present the user with content information, pertaining to each multiple choice question answered incorrectly, until the user answers the question correctly.

40. The method of claim 31 wherein the user interacts with the gaming portion using a cellular phone.

41. The method of claim 31 wherein the user interacts with the gaming portion using a kiosk.

42. The method of claim 31 wherein the user interacts with the gaming portion using a personal digital assistant.

43. The method of claim 31 wherein the user interacts with the gaming portion using a wireless device.

44. The method of claim 31 wherein the content of the educating portion is displayed on a dedicated website.

45. The method of claim 44 wherein the interactive portion provides a search feature of the website and the Internet.

46. The method of claim 31 wherein the interactive portion provides hyperlinks to websites related to the content material of the educating portion.

47. The method of claim 31 wherein the content material of the educating portion offers guidance for treatment of specific diseases.

48. The method of claim 31 wherein the content material of the educating portion offers guidance for treatment of specific medical conditions.

49. The method of claim 31 wherein the content material of the educating portion provides guidance for tracking standard healthy behaviors and their results.

50. The method of claim 31 wherein the content material of the educating portion displays procedures for performing a predefined set of disease-specific self-tests of body fluids.

51. The method of claim 31 wherein the content material of the educating portion displays guidelines for a predefined set of disease-specific medication dosages and contra-indications for these dosages.

52. The method of claim 31 wherein the alerting portion reads the information captured by the monitoring portion and tracks it.

53. The method of claim 52 wherein the alerting portion alerts the user when it is time to refill a prescription.

54. The method of claim 52 wherein the alerting portion notifies the user if the user fails to take the proper dosage in accordance with the prescription.

55. The method of claim 31 wherein the interactive portion provides the user with information and assistance stored by the educating portion.

56. The method of claim 55 wherein the information and assistance is directed at filing insurance claims.

57. The method of claim 55 wherein the user's personal information, self-improvement behavior input to the monitoring portion, and responses to the gaming portion are recorded by the recording portion.

58. The method of claim 57 wherein the information recorded is provided as a service to assist health, security and medical providers.

59. The method of claim 31 wherein the self-improvement behaviors input to the monitoring system are chosen from a set of standard nutrition, exercise, and medication wellness practices.

60. The method of claim 31 wherein the alerting portion notifies the user of contraindications to the medication dosage the user is taking.

* * * * *